(12) United States Patent
Takagi et al.

(10) Patent No.: US 12,343,329 B2
(45) Date of Patent: Jul. 1, 2025

(54) METHOD FOR SUPPRESSING PRODUCTION OF ASENAPINE-N-OXIDE

(71) Applicant: HISAMITSU PHARMACEUTICAL CO., INC., Tosu (JP)

(72) Inventors: Yuka Takagi, Tsukuba (JP); Masaki Yukuhiro, Tsukuba (JP)

(73) Assignee: HISAMITSU PHARMACEUTICAL CO., INC., Tosu (JP)

( * ) Notice: Subject to any disclaimer, the term of this patent is extended or adjusted under 35 U.S.C. 154(b) by 197 days.

(21) Appl. No.: 17/768,555

(22) PCT Filed: Oct. 19, 2020

(86) PCT No.: PCT/JP2020/039240
§ 371 (c)(1),
(2) Date: Apr. 13, 2022

(87) PCT Pub. No.: WO2021/085211
PCT Pub. Date: May 6, 2021

(65) Prior Publication Data
US 2024/0122898 A1 Apr. 18, 2024

(30) Foreign Application Priority Data

Oct. 28, 2019 (JP) ................................. 2019-195125
Mar. 31, 2020 (JP) ................................. 2020-063702

(51) Int. Cl.
*A61K 31/407* (2006.01)
*A61K 9/70* (2006.01)
*A61K 47/02* (2006.01)

(52) U.S. Cl.
CPC .......... *A61K 31/407* (2013.01); *A61K 9/7053* (2013.01); *A61K 47/02* (2013.01)

(58) Field of Classification Search
CPC .. A61K 31/407; A61K 9/7053; A61K 9/7038; A61P 25/00; A61P 25/18
See application file for complete search history.

(56) References Cited

U.S. PATENT DOCUMENTS

| | | | | |
|---|---|---|---|---|
| 11,850,311 | B2 * | 12/2023 | Yukuhiro | ............... A61K 47/12 |
| 2012/0089104 | A1 | 4/2012 | Wang et al. | |
| 2015/0202183 | A1 | 7/2015 | Suzuki et al. | |
| 2015/0231250 | A1 | 8/2015 | Sonobe et al. | |
| 2018/0193283 | A1 * | 7/2018 | Mohr | ................... A61K 9/7053 |

FOREIGN PATENT DOCUMENTS

| | | |
|---|---|---|
| CN | 107427472 A | 12/2017 |
| CN | 107847487 A | 3/2018 |
| CN | 107847488 A | 3/2018 |
| CN | 110087640 A | 8/2019 |
| CN | 110087641 A | 8/2019 |
| EP | 3861999 A1 | 8/2021 |
| JP | 201725111 A | 2/2017 |
| KR | 20170120181 A | 10/2017 |
| KR | 20190099230 A | 8/2019 |
| KR | 20190099231 A | 8/2019 |
| WO | 2005123046 A1 | 12/2005 |
| WO | 2014017595 A1 | 1/2014 |
| WO | 2014207664 A2 | 12/2014 |
| WO | 2016140087 A1 | 9/2016 |
| WO | 2017018321 A1 | 2/2017 |
| WO | 2017018322 A1 | 2/2017 |
| WO | 2018115001 A1 | 6/2018 |
| WO | 2018115010 A1 | 6/2018 |
| WO | 2019243432 A1 | 12/2019 |

OTHER PUBLICATIONS

Xu, et al. "Controlled Water Vapor Transmission Rate Promotes Wound-Healing Via Wound Re-Epithelialization and Contraction Enhancement"; Scientific Reports; Apr. 18, 2016.
Japanese Office Action dated Aug. 16, 2022 corresponding to application No. P2021-510472.
"Type of Rubber Material Overview, characteristics, and properties of all 18 materials ", Jun. 10, 2019.
International Preliminary Report on Patentability(IPRP) dated May 12, 2022 corresponding to application No. PCT/JP2020/039240.
International Search Report dated Dec. 22, 2020 corresponding to application No. PCT/JP2020/039240.
Office Action dated May 11, 2023 corresponding to JP Patent Application No. P2021-510472.
"Stability Testing of New Drug Substances and Products"; European Medicines Agency; Aug. 2003.

\* cited by examiner

*Primary Examiner* — Sue X Liu
*Assistant Examiner* — Nathan W Schlientz
(74) *Attorney, Agent, or Firm* — Nath, Goldberg & Meyer; Joshua B. Goldberg

(57) ABSTRACT

The present invention provides a patch comprising an adhesive layer on a backing, the adhesive layer comprising: asenapine or a pharmaceutically acceptable salt thereof; an adhesive base; and at least one selected from the group consisting of thiosulfates, sulfites, and pyrosulfites.

3 Claims, No Drawings

METHOD FOR SUPPRESSING PRODUCTION OF ASENAPINE-N-OXIDE

TECHNICAL FIELD

The present invention relates to a method for suppressing generation of asenapine-N-oxide.

BACKGROUND ART

Asenapine is a compound known as a therapeutic agent of central nervous system diseases, in particular, schizophrenia. In Japan, sublingual tablets of asenapine maleate salt (trade name: SYCREST) are distributed as a pharmaceutical containing asenapine. Sublingual administration is generally known as a route of administration that is less susceptible to the first pass effect. Thus, it is expected that even a compound having a relatively low metabolic stability upon being sublingually administered will exhibit a sufficient pharmacological effect. In recent years, development of asenapine-containing patches as a new formulation is investigated (for example, Patent Literatures 1 to 3).

Asenapine after being absorbed by the body undergoes metabolism to produce various metabolites. As main primary metabolites of asenapine, an N-demethylated form (N-desmethylasenapine), an N-oxidized form (asenapine-N-oxide), an 11-hydroxylated form (11-hydroxyasenapine), and an asenapine-N-glucuronide conjugate are known. These metabolites have been considered to have a lower contribution to the originally intended therapeutic effect because they have a lower affinity for the receptors to which asenapine binds or have lower transferability to the brain.

CITATION LIST

Patent Literature

Patent Literature 1: WO 2017/018321
Patent Literature 2: WO 2017/018322
Patent Literature 3: WO 2018/115001

SUMMARY OF INVENTION

Technical Problem

The present inventors have found that asenapine can be oxidized to generate asenapine-N-oxide in the process of manufacturing the patch. Thus, an object of the present invention is to provide a method for suppressing generation of asenapine-N-oxide. Another object of the present invention is to provide a patch in which the generation of asenapine-N-oxide is suppressed.

Solution to Problem

The present invention provides the following [1] to [12]:
[1] A patch comprising an adhesive layer on a backing, the adhesive layer comprising: asenapine or a pharmaceutically acceptable salt thereof; an adhesive base; and at least one selected from the group consisting of thiosulfates, sulfites, and pyrosulfites.
[2] The patch according to [1], wherein the pyrosulfite is sodium pyrosulfite or potassium pyrosulfite.
[3] The patch according to [1] or [2], wherein the adhesive base is a rubber adhesive base.
[4] The patch according to [1] or [2], wherein the adhesive base is an acrylic adhesive base or a silicone adhesive base, and the asenapine or the pharmaceutically acceptable salt thereof is asenapine maleate salt.
[5] A method for manufacturing a patch, the method comprising: adding at least one selected from the group consisting of thiosulfates, sulfites, and pyrosulfites to a composition comprising an adhesive base and asenapine or a pharmaceutically acceptable salt thereof to obtain an adhesive composition; and spreading the adhesive composition on the backing.
[6] The method for manufacturing the patch according to [5], wherein the pyrosulfite is sodium pyrosulfite or potassium pyrosulfite.
[7] The method for manufacturing the patch according to [5] or [6], wherein the adhesive base is a rubber adhesive base.
[8] The method for manufacturing the patch according to [5] or [6], wherein the adhesive base is an acrylic adhesive base or a silicone adhesive base, and the asenapine or the pharmaceutically acceptable salt thereof is asenapine maleate salt.
[9] A method for suppressing generation of asenapine-N-oxide, the method comprising: adding at least one selected from the group consisting of thiosulfates, sulfites, and pyrosulfites to a composition comprising an adhesive base and asenapine or a pharmaceutically acceptable salt thereof.
[10] The method according to [9], wherein the pyrosulfite is sodium pyrosulfite or potassium pyrosulfite.
[11] The method for suppressing the generation of asenapine-N-oxide according to [9] or [10], wherein the adhesive base is a rubber adhesive base.
[12] The method for suppressing the generation of asenapine-N-oxide according to [9] or [10], wherein the adhesive base is an acrylic adhesive base or a silicone adhesive base, and the asenapine or the pharmaceutically acceptable salt thereof is asenapine maleate salt.

Advantageous Effects of Invention

According to the present invention, it is possible to suppress generation of asenapine-N-oxide in the process of manufacturing the patch. According to the present invention, it is also possible to provide the patch in which the generation of asenapine-N-oxide is suppressed. The asenapine-containing patch of the present invention can withstand storage for a longer period of time because the generation of asenapine N-oxide is suppressed.

According to the findings of the present inventors, the degree of asenapine-N-oxide generation in the manufacturing process and storage process of the patch may vary depending on the type of the adhesive base. In particular, when an acrylic adhesive base or a silicone adhesive base is used as the adhesive base, asenapine-N-oxide tends to be more easily generated than when a rubber adhesive base is used.

Thus, in the present specification, "suppression of generation of asenapine-N-oxide in the process of manufacturing the patch" means that the generation amount of asenapine-N-oxide immediately after manufacture of the patch is 0.05% or less (preferably 0.03% or less) when the adhesive base is a rubber adhesive base, and means that the generation amount of asenapine-N-oxide immediately after manufacture of the patch is 90% or less (preferably 80% or less) when the adhesive base is an acrylic adhesive base or a silicone adhesive base, as compared with the numerical value in a patch containing only asenapine or a pharmaceutically acceptable salt thereof and the adhesive base (e.g., Comparative Examples 5 and 6).

Further, "suppression of generation of asenapine-N-oxide in the storage process of the patch" means that the generation amount of asenapine-N-oxide after storage of the patch at 60° C. for 2 weeks is 0.25% or less (preferably 0.20% or less) when the adhesive base is a rubber adhesive base, and means that the generation amount of asenapine-N-oxide after storage of the patch at 60° C. for 2 weeks is 90% or less (preferably 85% or less) when the adhesive base is an acrylic adhesive base or a silicone adhesive base, as compared with the numerical value in a patch containing only asenapine or a pharmaceutically acceptable salt thereof and the adhesive base (e.g., Comparative Examples 5 and 6).

DESCRIPTION OF EMBODIMENTS

The present invention will be described in detail below with showing embodiments of the present invention.

An embodiment of the present invention is a patch comprising an adhesive layer on a backing, the adhesive layer containing asenapine or a pharmaceutically acceptable salt thereof; an adhesive base; and at least one selected from the group consisting of thiosulfates, sulfites, and pyrosulfites.

The backing may be any backing which can maintain the form of the patch, in particular, the adhesive layer. Examples of the material of the backing include polyethylene, polypropylene, polybutadiene, an ethylene-vinyl chloride copolymer, polyvinyl chloride, polyamide such as nylon, polyester, a cellulose derivative, and a synthetic resin such as polyurethane. Examples of the shape of the backing include a film, a sheet, a sheet-like porous body, sheet-like foam, cloth such as woven fabric, knitted fabric and nonwoven fabric, and laminated products thereof. The thickness of the backing is not specifically limited, but it is preferable that the thickness of the backing be normally about 2 to 3000 μm.

The adhesive layer is formed from an adhesive composition obtained by mixing: asenapine or a pharmaceutically acceptable salt thereof; an adhesive base; at least one selected from the group consisting of thiosulfates, sulfites, and pyrosulfites; and optional components to be described below. The thickness of the adhesive layer is not specifically limited and may be 30 to 300 μm, 50 to 200 μm, or 70 to 120 μm. If the thickness of the adhesive layer is over 300 lam, the patch tends to easily fall off, for example when clothes are put on or off.

Asenapine is a compound which is also referred to as (3aRS,12bRS)-5-chloro-2-methyl-2,3,3a,12b-tetrahydro-1H-dibenzo[2, 3:6,7]oxepino[4,5-c]pyrrole and is represented by the following formula (1).

[Chemical Formula 1]

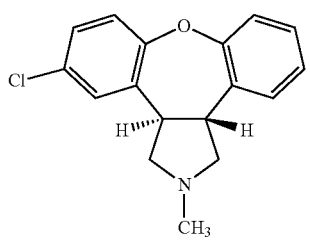

(1)

A pharmaceutically acceptable salt of asenapine refers to an acid addition salt of asenapine that can be used as a pharmaceutical. Examples of the acid include hydrochloric acid, hydrobromic acid, hydroiodic acid, phosphoric acid, acetic acid, propionic acid, glycolic acid, maleic acid, malonic acid, succinic acid, tartaric acid, citric acid, ascorbic acid, salicylic acid and benzoic acid. For example, asenapine maleate is commercially available as a therapeutic agent of schizophrenia.

Asenapine encompasses a plurality of optical isomers and may be any optical isomer and may be a mixture of optical isomers such as a racemate. The acid added to asenapine is not specifically limited as long as it is pharmaceutically acceptable. The acid addition salt of asenapine may be anhydride or hydrate.

The content of asenapine or a pharmaceutically acceptable salt thereof may be 1 to 30% by mass and is preferably 2 to 20% by mass or 3 to 10% by mass relative to the total mass of the adhesive layer.

The adhesive base is a component which gives adhesiveness to an adhesive layer, and examples of the adhesive base include a rubber adhesive base, an acrylic adhesive base and a silicone adhesive base. It is preferable that the adhesive base be one or more selected from the group consisting of a rubber adhesive base, an acrylic adhesive base and a silicone adhesive base. It is preferable that the adhesive base be free of water (a nonaqueous adhesive base). The adhesive base may be any one of a rubber adhesive base, an acrylic adhesive base and a silicone adhesive base, or may be a combination thereof. It is preferable that the total content of the adhesive base be 40 to 98% by mass relative to the total mass of the adhesive layer, and it is more preferable that the total content of the adhesive base be 50 to 95% by mass.

Examples of the rubber adhesive base include natural rubber, polyisobutylene, an alkyl vinyl ether (co)polymer, polyisoprene, polybutadiene, styrene-butadiene copolymer, styrene-isoprene copolymer and a styrene-isoprene-styrene block copolymer. One of these rubber adhesive bases may be used alone or two or more may be used in combination. Among these, it is preferable that the rubber adhesive base related to the present embodiment be at least one selected from the group consisting of a styrene-isoprene-styrene block copolymer and polyisobutylene, and it is more preferable that the rubber adhesive related to the present invention be a styrene-isoprene-styrene block copolymer and polyisobutylene, from the viewpoint that it tends to be possible to achieve more sufficient adhesion of the adhesive layer.

Specific examples of the rubber adhesive include Oppanol B12, B15, B50, B80, B100, B120, B150 and B220 (trade name, manufactured by BASF), JSR BUTYL 065, 268 and 365 (trade name, manufactured by JSR Corporation), Vistanex LM-MS, MH, H, MML-80, 100, 120 and 140 (trade name, manufactured by Exxon Chemicals), HYCAR (trade name, manufactured by Goodrich Corporation), and SIBSTAR T102 (trade name, manufactured by Kaneka Corporation).

The content of the rubber adhesive base may be 10 to 90% by mass or may be 15 to 85% by mass relative to the total mass of the adhesive layer.

The acrylic adhesive base is a component which gives adhesiveness to an adhesive layer, and examples of the acrylic adhesive base include (co)polymers of one or two or more types of (meth)acrylic acid alkyl ester. Examples of the (meth)acrylic acid alkyl ester include butyl (meth)acrylate, isobutyl (meth)acrylate, hexyl (meth)acrylate, octyl (meth)acrylate, 2-ethylhexyl (meth)acrylate and decyl (meth)acrylate. In the specification, the term "(meth)acrylic acid" refers to either one or both of acrylic acid and methacrylic acid, and similar expressions are defined in a same manner. When the adhesive base is the acrylic adhesive base, use of asenapine maleate salt is less likely to suppress the generation of asenapine-N-oxide than use of asenapine free base.

The acrylic adhesive base may be a copolymer formed from (meth)acrylic acid alkyl ester (a main monomer) and a comonomer. Examples of the main monomer include methyl (meth)acrylate, ethyl (meth)acrylate, butyl (meth)acrylate, hexyl (meth)acrylate, heptyl (meth)acrylate, octyl (meth) acrylate and 2-ethylhexyl (meth)acrylate, and one of these may be used alone or two or more may be used in combination. The comonomer may be any component which can copolymerize with (meth)acrylic acid alkyl ester. Examples of the comonomer include (meth)acrylic acid hydroxyalkyl ester, ethylene, propylene, styrene, vinyl acetate, N-vinylpyrrolidone, (meth)acrylic acid and amide (meth)acrylate. One of these comonomers may be used alone or two or more may be used in combination.

Specific examples of the acrylic adhesive base include an acrylic acid-acrylic acid octyl ester copolymer, a 2-ethylhexyl acrylate-vinylpyrrolidone copolymer solution, an acrylic acid ester-vinyl acetate copolymer, a 2-ethylhexyl acrylate-2-ethylhexyl methacrylate-dodecyl methacrylate copolymer, a methyl acrylate-2-ethylhexyl acrylate copolymer resin emulsion, and an acrylic polymer contained in an acrylic resin alkanolamine solution. Specific examples of such acrylic adhesives include a series of DURO-TAK such as DURO-TAK(Registered trademark) 387-2510, DURO-TAK(Registered trademark) 87-2510, DURO-TAK(Registered trademark) 387-2287, DURO-TAK(Registered trademark) 87-2287, DURO-TAK(Registered trademark) 87-4287, DURO-TAK(Registered trademark) 387-2516, DURO-TAK(Registered trademark) 87-2516, DURO-TAK (Registered trademark) 87-2074, DURO-TAK(Registered trademark) 87-900A, DURO-TAK(Registered trademark) 87-901A, DURO-TAK(Registered trademark) 87-9301 and DURO-TAK(Registered trademark) 87-4098 (manufactured by Henkel); a series of GELVA such as GELVA(Registered trademark) GMS 788, GELVA(Registered trademark) GMS 3083 and GELVA(Registered trademark) GMS 3253 (manufactured by Henkel); a series of MAS such as MAS811 (trade name) and MAS683 (trade name) (manufactured by CosMED Pharmaceuticals); a series of EUDRAGIT(Registered trademark, manufactured by Evonik Industries AG), NICAZOLE (Registered trademark, manufactured by NIPPON CARBIDE INDUSTRIES CO., INC.) and ULTRAZOLE (Registered trademark, manufactured by Aica Kogyo Co., Ltd.).

The content of the acrylic adhesive base may be 10 to 90% by mass or may be 15 to 85% by mass relative to the total mass of the adhesive layer.

The silicone adhesive base is a compound having an organopolysiloxane backbone. Examples of the silicone adhesive base include dimethylpolysiloxane, polymethylvinylsiloxane, and polymethylphenylsiloxane. Specific examples of the silicone adhesive base include a series of MD such as MD7-4502 Silicone Adhesive and MD7-4602 Silicone Adhesive (manufactured by Dow Corning Corp.); a series of BIO-PSA such as BIO-PSA(Registered trademark) 7-4301 Silicone Adhesive, BIO-PSA(Registered trademark) 7-4302 Silicone Adhesive, BIO-PSA(Registered trademark) 7-4201 Silicone Adhesive, BIO-PSA(Registered trademark) 7-4202 Silicone Adhesive, BIO-PSA(Registered trademark) 7-4101 Silicone Adhesive, BIO-PSA(Registered trademark) 7-4102 Silicone Adhesive, BIO-PSA(Registered trademark) 7-4601 Silicone Adhesive, BIO-PSA(Registered trademark) 7-4602 Silicone Adhesive, BIO-PSA(Registered trademark) 7-4501 Silicone Adhesive, BIO-PSA(Registered trademark) 7-4502 Silicone Adhesive, BIO-PSA(Registered trademark) 7-4401 Silicone Adhesive and BIO-PSA(Registered trademark) 7-4402 Silicone Adhesive (manufactured by Dow Corning Corp.), Dow Corning(Registered trademark) 7-9800A, Dow Corning(Registered trademark) 7-9800B, Dow Corning(Registered trademark) 7-9700A and Dow Corning(Registered trademark) 7-9700B. When the adhesive base is the silicone adhesive base, use of asenapine maleate salt is less likely to suppress the generation of asenapine-N-oxide than use of asenapine free base.

The content of the silicone adhesive base may be 10 to 90% by mass or may be 15 to 85% by mass relative to the total mass of the adhesive layer.

The adhesive layer and the adhesive composition contain at least one selected from the group consisting of thiosulfates, sulfites, and pyrosulfites.

The thiosulfate is not specifically limited as long as it is a metal salt of thiosulfuric acid. The thiosulfate is preferably an alkali metal salt of thiosulfuric acid, more preferably sodium thiosulfate or potassium thiosulfate. The content of the thiosulfate may be 0.005 to 1% by mass and is preferably 0.01 to 0.8% by mass or 0.02 to 0.5% by mass relative to the total mass of the adhesive layer. When the content of the thiosulfate is 0.02% by mass or more, the generation of asenapine-N-oxide can be further suppressed.

The sulfite is not specifically limited as long as it is a metal salt of sulfurous acid. The sulfite is preferably an alkali metal salt of sulfurous acid, more preferably sodium sulfite, sodium bisulfite, potassium sulfite, or potassium bisulfite. The content of the sulfite may be 0.005 to 1% by mass and is preferably 0.01 to 0.8% by mass or 0.02 to 0.5% by mass relative to the total mass of the adhesive layer. When the content of the sulfite is 0.02% by mass or more, the generation of asenapine-N-oxide can be further suppressed.

The pyrosulfite is not specifically limited as long as it is a metal salt of pyrosulfurous acid. The pyrosulfite is preferably an alkali metal salt of pyrosulfurous acid, more preferably sodium pyrosulfite or potassium pyrosulfite. The content of the pyrosulfite may be 0.005 to 1% by mass and is preferably 0.01 to 0.8% by mass or 0.02 to 0.5% by mass relative to the total mass of the adhesive layer. When the content of the pyrosulfite is 0.02% by mass or more, the generation of asenapine-N-oxide can be further suppressed.

The adhesive layer may optionally further contain other additives. Examples of the other additives include a tackifier resin, a plasticizer, an absorption promoting agent, a resolvent, other auxiliary stabilizing agents, fillers and flavors.

The tackifier resin is a component that adjusts the adhesiveness of the adhesive layer. Examples of the tackifier resin include an alicyclic saturated hydrocarbon resin; rosin and rosin derivatives such as glycerine ester of rosin, hydrogenated rosin, glycerine ester of hydrogenated rosin, pentaerythritol ester of rosin and maleated rosin; a terpene tackifier resin; a petroleum tackifier resin. One of the tackifier resins may be used alone or two or more may be used in combination. When the adhesive layer contains the tackifier resin, the content of the tackifier resin is, for example, 2 to 65% by mass, 5 to 60% by mass, or 10 to 55% by mass relative to the total mass of the adhesive layer.

Examples of the plasticizer include paraffin oil (liquid paraffin, etc.), squalane, squalene, vegetable oils (olive oil, camellia oil, castor oil, tall oil, peanut oil, spearmint oil, eucalyptus oil, jojoba oil, camphor white oil, sunflower oil, orange oil, etc.), fats and oils (dibutyl phthalate, dioctyl phthalate, etc.), and liquid rubbers (liquid polybutene, liquid isoprene rubber, etc.). Preferred plasticizer is liquid paraffin or liquid polybutene. When the adhesive layer contains the plasticizer, the content of the plasticizer is, for example, 3 to 50% by mass, 5 to 30% by mass, or 7 to 20% by mass with respect to the total mass of the adhesive layer.

The absorption promoting agent may be any compound known to have a percutaneous absorption promoting effect. Examples of the absorption promoting agent include organic acids and salts thereof (e.g., aliphatic carboxylic acids having 6 to 20 carbon atoms (hereinafter also referred to as "fatty acids") and salts thereof, cinnamic acids and salts thereof), organic acid esters (e.g., fatty acid esters, cinnamic acid esters), organic acid amides (e.g., fatty acid amides), fatty alcohols, polyhydric alcohols, and ethers (e.g., fatty ethers, polyoxyethylene alkyl ethers). These absorption promoting agents may have unsaturated bonds and may have a cyclic, linear or branched chemical structure. The absorption promoting agent may also be a monoterpene compound, a sesquiterpene compound, and a vegetable oil (e.g., olive oil). One of these absorption promoting agents may be used alone or two or more may be used in combination.

Examples of such organic acids include aliphatic (mono-, di- or tri-) carboxylic acids (e.g., acetic acid, propionic acid, citric acid (including anhydrous citric acid), isobutyric acid, caproic acid, caprylic acid, fatty acids, lactic acid, maleic acid, pyruvic acid, oxalic acid, succinic acid, tartaric acid), aromatic carboxylic acids (e.g., phthalic acid, salicylic acid, benzoic acid, acetylsalicylic acid), cinnamic acid, alkanesulfonic acids (e.g., methanesulfonic acid, ethanesulfonic acid, propanesulfonic acid, butanesulfonic acid), alkylsulfonic acid derivatives (e.g., polyoxyethylene alkyl ether sulfonic acid, N-2-hydroxyethylpiperazine-N'-2-ethanesulfonic acid), and cholic acid derivatives (e.g. dehydrocholic acid). These organic acids may be alkali metal salts such as sodium salts. Among them, an aliphatic carboxylic acid, an aromatic carboxylic acid, or a salt thereof is preferable, and acetic acid, sodium acetate, or citric acid is particularly preferable. Examples of the fatty acids include lauric acid, myristic acid, palmitic acid, stearic acid, isostearic acid, oleic acid, linoleic acid, and linolenic acid.

Examples of the organic acid esters include ethyl acetate, propyl acetate, cetyl lactate, lauryl lactate, methyl salicylate, ethylene glycol salicylate, methyl cinnamate, and fatty acid esters. Examples of the fatty acid esters include methyl laurate, hexyl laurate, isopropyl myristate, myristyl myristate, octyldodecyl myristate, isopropyl palmitate, and cetyl palmitate. The fatty acid esters may be glycerin fatty acid ester, propylene glycol fatty acid ester, sorbitan fatty acid ester, polyethylene glycol sorbitan fatty acid ester, polyethylene glycol fatty acid ester, sucrose fatty acid ester, or polyoxyethylene hydrogenated castor oil. Specific examples of the fatty acid ester include glycerin monocaprylate, glycerin monocaprate, glycerin monolaurate, glycerin monooleate, sorbitan monolaurate, sucrose monolaurate, Polysorbate 20 (trade name), propyleneglycol monolaurate, polyethyleneglycol monolaurate, polyethyleneglycol monostearate, Span20, Span40, Span60, Span80, Span120 (trade name), Tween20, Tween21, Tween40, Tween60, Tween80 (trade name), and NIKKOL HCO-60 (trade name).

Examples of the organic amides include fatty amides (e.g., lauric diethanolamide), hexahydro-1-dodecyl-2H-azepine-2-one (also referred to as Azone) and derivatives thereof, and pyrrothiodecane.

The fatty alcohol refers to an aliphatic alcohol having 6 to 20 carbon atoms. Examples of the fatty alcohols include lauryl alcohol, myristyl alcohol, oleyl alcohol, isostearyl alcohol, and cetyl alcohol. Examples of the polyhydric alcohols include propylene glycol.

The fatty ether refers to an ether having an aliphatic group (e.g., an alkyl group or an alkenyl group) having 6 to 20 carbon atoms. Examples of the polyoxyethylene alkyl ethers include polyoxyethylene lauryl ether.

Examples of the monoterpene compound include geraniol, thymol, eugenol, terpineol, 1-menthol, borneol, d-limonene, isoeugenol, isoborneol, nerol, and dl-camphor. Mentha oil may be used as the monoterpene compound.

The absorption promoting agent is more preferably a fatty acid (particularly oleic acid), isopropyl palmitate, oleyl alcohol, lauryl alcohol, isostearyl alcohol, lauric acid diethanolamide, glycerin monocaprylate, glycerin monocaprate, glycerin monooleate, sorbitan monolaurate, propylene glycol monolaurate, polyoxyethylene lauryl ether, or pyrothiodecane.

When the adhesive layer contains the absorption promoting agent, it is preferable that the content of the absorption promoting agent be 2 to 40% by mass relative to the total mass of the adhesive layer. When the content of the absorption promoting agent is 2% by mass or more, asenapine will have its skin permeability further increased and tends to exhibit a sufficient pharmacological action. When the content of the absorption promoting agent is 40% by mass or less, skin irritancy tends not to be exhibited.

The resolvent is a component that facilitates the dissolution of asenapine or a pharmaceutically acceptable salt thereof in the adhesive composition. Examples of the resolvent include fatty acids (e.g., capric acid, oleic acid, linoleic acid), fatty acid alkyl esters (e.g., isopropyl myristate, isopropyl palmitate), fatty acid polyhydric alcohol esters (e.g., propylene glycol monolaurate, glycerin monolaurate, glycerin monooleate, sorbitan monolaurate), fatty acid amides (e.g., lauric diethanolamide), aliphatic alcohols (e.g., octyldodecanol, isostearyl alcohol, oleyl alcohol), polyhydric alcohols (e.g., propylene glycol, dipropylene glycol, polyethylene glycol), pyrrolidone derivatives (e.g., N-methyl-2-pyrrolidone), and organic acids or salts thereof (e.g., acetic acid, lactic acid, sodium acetate, sodium lactate). When the adhesive layer contains the resolvent, it is preferable that the content of the resolvent be 2 to 40% by mass relative to the total mass of the adhesive layer.

Other auxiliary stabilizing agents may be any agent that can suppress the formation of free radicals generated by the action of light rays such as ultraviolet rays, heat, or active chemical species and the progress of a chain reaction thereof. The stabilizing agent optionally contained can further improve the stability of asenapine in manufacturing the patch. Examples of the stabilizing agent include tocopherol and ester derivatives thereof, ascorbic acid and ester derivatives thereof, 2,6-dibutylhydroxytoluene (BHT), 2,6-dibutylhydroxyanisole (BHA), and 2-mercaptobenzimidazole. One of the stabilizing agents may be used alone or two or more may be used in combination. It is preferable that the stabilizing agent be dibutylhydroxytoluene because it allows the patch to have appropriate physical properties (formability, appearance, etc.) and makes asenapine more stable. When the adhesive layer contains the stabilizing agent, it is preferable that the content of the stabilizing agent be 0.1 to 3% by mass relative to the total mass of the adhesive layer, and it is more preferable that the content of the stabilizing agent be 0.1 to 1% by mass. When the content of the stabilizing agent is 0.1 to 3% by mass, the stability of each component in the patch tends to be excellent. The adhesive layer according to the present embodiment may not contain tocopherol, ascorbyl palmitate, or either of them.

Examples of the fillers include powders of metal compounds (aluminum oxide, aluminum hydroxide, zinc oxide, titanium oxide, calcium carbonate, etc.), ceramics (talc, clay, kaolin, silica, hydroxyapatite, synthetic aluminum silicate, magnesium aluminometasilicate, etc.) or organic compounds (cellulose powder, stearates, etc.), or short fibers of resins containing these. When the adhesive layer contains the filler, it is preferable that the content of the filler be 0.1 to 20% by mass relative to the total mass of the adhesive layer.

The patch may further comprise a release liner. The release liner is laminated on the side opposite to the backing on the adhesive layer. When the patch comprises a release liner, the deposition of dirt etc. onto the adhesive layer tents to be reduced during storage. The surface of the release liner in contact with the adhesive layer is preferably subjected to a release treatment with silicone, fluorinated polyolefin or the like.

The raw material of the release liner is not specifically limited, and liners generally known to those in the art may be used. Examples of the release liner include films of polyesters such as polyethylene terephthalate and polyethylene naphthalate; polyolefins such as polyethylene and polypropylene; polyvinyl chloride, polyvinylidene chloride, Nylon (trade name), and aluminum. The release liner may be a laminated film of fine quality paper and polyolefin. It is preferable that the material of the release liner be a film made of polypropylene or polyethylene terephthalate.

The patch can be manufactured, for example, by the following method, but is not limited thereto, and a known method can be used. First, components constituting the adhesive layer are mixed at a predetermined ratio to obtain a homogeneous solution (adhesive composition). Next, the adhesive composition is spread at a predetermined thickness on a releasable film (release liner) to form an adhesive layer. Further, a backing is pressure-bonded to the adhesive layer such that the adhesive layer is interposed between the release liner and the backing. Finally, the resultant is cut into a desired shape and dimensions, whereby the patch can be obtained. In this case, the release liner is removed upon application of the patch. The shape and dimensions of the patch may be, for example, a rectangle having a short side of 3 to 14 cm and a long side of 7 to 20 cm, or a circle having a diameter of 1 to 10 cm.

Examples

Preparation of Patch

In the following examples, unless otherwise indicated, patches were prepared as follows.

Components of each adhesive layer shown in Tables 1 to 7 were mixed and spread on a release-treated PET film (a release liner) to form an adhesive layer having a thickness of 100 lam (100 g/m 2). Next, a backing was pressure-bonded onto the adhesive layer, and then cut into an appropriate size to obtain a patch.

(Measurement of an Asenapine-N-Oxide Content)

The content of asenapine-N-oxide was measured by the following procedure using a patch immediately after manufacture and a patch after storage at 60° C. for two weeks or one month after manufacture.

First, the adhesive layer of the patch was taken out and immersed in 10 mL of tetrahydrofuran (grade for high performance liquid chromatography) to extract organic substances. Next, 5 mL of the obtained extract was collected, and a dilution solution (0.05% phosphoric acid aqueous solution/methanol=50/50 (v/v)) was added thereto to make the total amount 25 mL, and then insoluble matter was filtered out. After the filtrate was concentrated, a chromatogram in which peaks for asenapine and asenapine-N-oxide were separated was obtained by high performance liquid chromatography under the following analysis conditions. The content of asenapine-N-oxide was calculated by dividing the value of the area under the curve of the peak corresponding to asenapine-N-oxide by the value of the area under the curve of the peak corresponding to asenapine in the obtained chromatogram. That is, the amount of asenapine-N-oxide (also simply referred to as "N-oxide") shown in the table below is a relative value to the amount of asenapine. Note that the relative retention time (RRT) of asenapine-N-oxide to asenapine was 0.24.

<Analysis Conditions>

Column: CAPCELLPAKC18 MGII 5 μm (4.6 mm I.D× 150 mm)

Mobile phases: Methanol/phosphate buffer (pH 6.8)=70/30

Measurement wavelength: 230 nm

Flow rate: 1.0 mL/min

Sample injection amount: 15 μL

Column temperature: 50° C.

(Measurement of an Asenapine Content)

Using the chromatogram obtained above, the value of the area under the curve of asenapine contained in the patch after storage was divided by the value of the area under the curve of asenapine contained in the patch immediately after manufacture to calculate the amount of change in asenapine content. That is, the amount of asenapine shown in the following table is a relative value to the amount of asenapine in the patch immediately after manufacture.

TABLE 1

|  | Ref. Ex. 1 | Ref. Ex. 2 | Ref. Ex. 3 | Ref. Ex. 4 | Ref. Ex. 5 | Ref. Ex. 6 |
| --- | --- | --- | --- | --- | --- | --- |
| Asenapine maleate salt | 4.50 | 4.50 | 4.50 | 4.50 | 4.50 | 4.50 |
| Sodium acetate | 3.68 | 3.68 | 3.68 | 3.68 | 3.68 | 3.68 |
| Rubber adhesive base | 19.03 | 19.02 | 19.01 | 18.98 | 18.96 | 18.91 |
| Alicyclic saturated hydrocarbon resin | 55.18 | 55.15 | 55.11 | 55.05 | 54.98 | 54.85 |
| Liquid paraffin | 7.61 | 7.60 | 7.60 | 7.59 | 7.58 | 7.56 |
| BHT | — | 0.05 | 0.10 | 0.20 | 0.30 | 0.50 |
| Isopropyl palmitate | 10.00 | 10.00 | 10.00 | 10.00 | 10.00 | 10.00 |
| Total | 100 | 100 | 100 | 100 | 100 | 100 |
| N-oxide (immediately after manufacture) | 0.17 | 0.17 | 0.16 | 0.16 | 0.15 | 0.16 |
| N-oxide (60° C., one month) | 0.39 | 0.36 | 0.39 | 0.27 | 0.37 | 0.39 |

As shown in Table 1, even when 2,6-dibutylhydroxytoluene (BHT) was added as a stabilizing agent in manufacturing a patch containing asenapine maleate salt and a rubber adhesive base, asenapine-N-oxide was generated immediately after the manufacturing (Reference Example 2). Increasing the content of BHT did not decrease the amount of asenapine-N-oxide (Reference Examples 3 to 6). Note that the rubber adhesive bases for Reference Examples 1 to 6 were a mixture of SIS and polyisobutylene.

As shown in Table 2, asenapine-N-oxide was also generated in the patches of Comparative Examples 1 to 3. The patch of Comparative Example 4 had a small amount of asenapine-N-oxide generated immediately after manufacture but had a significantly increased amount of asenapine-N-oxide generated after storage at 60° C. for two weeks.

TABLE 2

|  | Comp. Ex. 1 | Comp. Ex. 2 | Comp. Ex. 3 | Comp. Ex. 4 |
|---|---|---|---|---|
| Asenapine maleate salt | 7.00 | 7.00 | 7.00 | 7.00 |
| Sodium acetate | 5.72 | 5.72 | 5.72 | 5.72 |
| SIS | 12.54 | 12.50 | 12.42 | 12.50 |
| Polyisobutylene | 5.37 | 5.36 | 5.32 | 5.36 |
| Alicyclic saturated hydrocarbon resin | 51.95 | 51.78 | 51.44 | 51.78 |
| Liquid paraffin | 7.17 | 7.14 | 7.10 | 7.14 |
| BHT | 0.25 | 0.50 | 1.00 | — |
| α-Tocopherol | — | — | — | 0.50 |
| Isopropyl palmitate | 10.00 | 10.00 | 10.00 | 10.00 |
| Total | 100 | 100 | 100 | 100 |
| N-oxide immediately after manufacture | 0.10 | 0.10 | 0.10 | 0.04 |
| N-oxide (60° C., two weeks) | 0.29 | 0.33 | 0.31 | 0.72 |
| Asenapine (60° C., two weeks) | 97.3 | — | — | 94.5 |

TABLE 3

|  | Ex. 9 | Ex. 1 | Ex. 2 | Ex. 3 | Ex. 4 |
|---|---|---|---|---|---|
| Asenapine maleate salt | 7.00 | 7.00 | 7.00 | 7.00 | 7.00 |
| Sodium acetate | 5.72 | 5.72 | 5.72 | 5.72 | 5.72 |
| SIS | 12.58 | 12.58 | 12.57 | 12.57 | 12.56 |
| Polyisobutylene | 5.39 | 5.39 | 5.39 | 5.39 | 5.38 |
| Alicyclic saturated hydrocarbon resin | 52.115 | 52.10 | 52.08 | 52.04 | 52.01 |
| Liquid paraffin | 7.19 | 7.19 | 7.19 | 7.18 | 7.18 |
| Isopropyl palmitate | 10.00 | 10.00 | 10.00 | 10.00 | 10.00 |
| Sodium pyrosulfite | 0.005 | 0.02 | 0.05 | 0.10 | 0.15 |
| Total | 100 | 100 | 100 | 100 | 100 |
| N-oxide (immediately after manufacture) | 0.02 | 0 | 0 | 0 | 0 |
| N-oxide (60° C., two weeks) | 0.14 | 0 | 0 | 0 | 0 |
| Asenapine (60° C., two weeks) | 95.9 | 96.1 | 96.6 | 97.3 | 96.4 |

TABLE 4

|  | Comp. Ex. 1 | Ex. 10 | Ex. 5 | Ex. 6 | Ex. 7 | Ex. 8 |
|---|---|---|---|---|---|---|
| Asenapine maleate salt | 7.00 | 7.00 | 7.00 | 7.00 | 7.00 | 7.00 |
| Sodium acetate | 5.72 | 5.72 | 5.72 | 5.72 | 5.72 | 5.72 |
| SIS | 12.54 | 12.539 | 12.54 | 12.52 | 12.52 | 12.46 |
| Polyisobutylene | 5.37 | 5.374 | 5.37 | 5.37 | 5.36 | 5.34 |
| Alicyclic saturated hydrocarbon resin | 51.95 | 51.947 | 51.94 | 51.88 | 51.84 | 51.61 |
| Liquid paraffin | 7.17 | 7.165 | 7.16 | 7.16 | 7.16 | 7.12 |
| BHT | 0.25 | 0.25 | 0.25 | 0.25 | 0.25 | 0.25 |
| Isopropyl palmitate | 10.00 | 10.00 | 10.00 | 10.00 | 10.00 | 10.00 |
| Sodium pyrosulfite | — | 0.005 | 0.02 | 0.10 | 0.15 | 0.50 |
| Total | 100 | 100 | 100 | 100 | 100 | 100 |
| N-oxide (immediately after manufacture) | 0.10 | 0.03 | 0 | 0 | 0 | 0 |
| N-oxide (60° C., two weeks) | 0.29 | 0.17 | 0 | 0 | 0 | 0 |
| Asenapine (60° C., two weeks) | 97.3 | — | 96.2 | 96.7 | 100.3 | 97.8 |

As shown in Tables 3 and 4, when pyrosulfite was added instead of BHT (Examples 1 to 4), the generation of asenapine-N-oxide was significantly suppressed immediately after manufacture, and even after storage at 60° C. for two weeks, asenapine-N-oxide was not generated. Further, Examples 5 to 8 (combined use of BHT and pyrosulfite) showed a tendency that the decrease in the asenapine content was further suppressed.

TABLE 5

|  | Ex. 11 | Ex. 12 | Ex. 13 | Ex. 14 | Ex. 15 | Ex. 16 |
|---|---|---|---|---|---|---|
| Asenapine maleate salt | 7.00 | 7.00 | 7.00 | 7.00 | 7.00 | 7.00 |
| Sodium acetate | 5.72 | 5.72 | 5.72 | 5.72 | 5.72 | 5.72 |
| SIS | 12.58 | 12.58 | 12.50 | 12.58 | 12.58 | 12.50 |
| Polyisobutylene | 5.39 | 5.39 | 5.36 | 5.39 | 5.39 | 5.36 |
| Alicyclic saturated hydrocarbon resin | 52.115 | 52.10 | 51.78 | 52.115 | 52.10 | 51.78 |
| Liquid paraffin | 7.19 | 7.19 | 7.14 | 7.19 | 7.19 | 7.14 |
| Isopropyl palmitate | 10.00 | 10.00 | 10.00 | 10.00 | 10.00 | 10.00 |
| Sodium thiosulfate | 0.005 | 0.02 | 0.50 | — | — | — |
| Sodium bisulfite | — | — | — | 0.005 | 0.02 | 0.50 |
| Total | 100 | 100 | 100 | 100 | 100 | 100 |
| N-oxide (immediately after manufacture) | 0.03 | 0 | 0 | 0 | 0 | 0 |
| N-oxide (60° C., two weeks) | 0.11 | 0.06 | 0 | 0.15 | 0.07 | 0.02 |
| Asenapine (60° C., two weeks) | 96.5 | 94.2 | 96.8 | 96.4 | 96.7 | 95.7 |

As shown in Table 5, the generation of asenapine-N-oxide was suppressed even when sodium thiosulfate or sodium bisulfite was used instead of sodium pyrosulfite.

TABLE 6

|  | Ex. 17 | Ex. 18 | Ex. 19 |
|---|---|---|---|
| Asenapine (as free base) | 5.00 | 5.00 | 5.00 |
| SIS | 13.84 | 13.83 | 13.76 |
| Polyisobutylene | 5.93 | 5.93 | 5.89 |
| Alicyclic saturated hydrocarbon resin | 57.315 | 57.31 | 56.99 |
| Liquid paraffin | 7.91 | 7.91 | 7.86 |
| Isopropyl palmitate | 10.00 | 10.00 | 10.00 |
| Sodium pyrosulfite | 0.005 | 0.02 | 0.50 |
| Total | 100 | 100 | 100 |
| N-oxide (immediately after manufacture) | 0 | 0 | 0 |
| N-oxide (60° C., two weeks) | 0 | 0 | 0 |
| Asenapine (60° C., two weeks) | 93.1 | 96.5 | 97.2 |

As shown in Table 6, the generation of asenapine-N-oxide was suppressed even when asenapine free base was used instead of asenapine maleate salt.

TABLE 7

|  | Comp. Ex. 5 | Ex. 20 | Ex. 21 | Comp. Ex. 6 | Ex. 22 | Ex. 23 |
|---|---|---|---|---|---|---|
| Asenapine maleate salt | 7.00 | 7.00 | 7.00 | 7.00 | 7.00 | 7.00 |
| Sodium acetate | 5.72 | 5.72 | 5.72 | 5.72 | 5.72 | 5.72 |
| DURO-TAK 87-4287 | 87.28 | 87.26 | 86.78 | — | — | — |
| BIO-PSA 7-4202 | — | — | — | 87.28 | 87.26 | 86.78 |
| Sodium pyrosulfite | — | 0.02 | 0.50 | — | 0.02 | 0.50 |
| Total | 100 | 100 | 100 | 100 | 100 | 100 |
| N-oxide (immediately after manufacture) | 0.62 | 0.41 | 0.28 | 0.81 | 0.6 | 0.13 |
| N-oxide (60° C., two weeks) | 4.19 | 3.54 | 1.08 | 3.95 | 3.29 | 2.02 |
| Asenapine (60° C., two weeks) | 94.9 | 93.6 | 97.2 | 90.2 | 90.2 | 93.0 |

As shown in Table 7, the generation of asenapine-N-oxide was suppressed even when an acrylic adhesive base or a silicone adhesive base was used instead of the rubber adhesive base.

The invention claimed is:

1. A patch comprising an adhesive layer on a backing, the adhesive layer comprising:
    3 to 10% by mass relative to the total mass of the adhesive layer of asenapine or a pharmaceutically acceptable salt thereof;
    an adhesive base; and
    0.02 to 1% by mass relative to the total mass of the adhesive layer of at least one component selected from the group consisting of thiosulfates, sulfites, and pyrosulfites;
    wherein the adhesive base is a rubber-based adhesive base consisting of a styrene-isoprene-styrene block copolymer and polyisobutylene.

2. A method for manufacturing a patch, the method comprising:
    adding at least one component selected from the group consisting of thiosulfates, sulfites, and pyrosulfites to a composition comprising an adhesive base and asenapine or a pharmaceutically acceptable salt thereof to obtain an adhesive composition, wherein the adhesive composition comprises 0.02 to 1% by mass relative to the total mass of the adhesive layer of the at least one component, and 3 to 10% by mass relative to the total mass of the adhesive layer of the asenapine or a pharmaceutically acceptable salt thereof; and spreading the adhesive composition on a backing;

wherein the adhesive base is a rubber-based adhesive base consisting of a styrene-isoprene-styrene block copolymer and polyisobutylene.

3. A method for suppressing generation of asenapine-N-oxide, the method comprising:

adding at least one component selected from the group consisting of thiosulfates, sulfites, and pyrosulfites to a composition comprising an adhesive base and asenapine or a pharmaceutically acceptable salt thereof;

wherein the adhesive composition comprises 0.02 to 1% by mass relative to the total mass of the adhesive layer of the at least one component, and 3 to 10% by mass relative to the total mass of the adhesive layer of the asenapine or a pharmaceutically acceptable salt thereof; and wherein the adhesive base is a rubber-based adhesive base consisting of a styrene-isoprene-styrene block copolymer and polyisobutylene.

* * * * *